United States Patent
Jack et al.

(10) Patent No.: US 9,326,524 B1
(45) Date of Patent: May 3, 2016

(54) INSECT REPELLENT COMPOSITIONS

(71) Applicants: Nancy Jack, Wilton, CT (US); Jeffrey Busch, Wilton, CT (US)

(72) Inventors: Nancy Jack, Wilton, CT (US); Jeffrey Busch, Wilton, CT (US)

(73) Assignee: Nantucket Spider, LLC, Wilton, CT (US)

( * ) Notice: Subject to any disclaimer, the term of this patent is extended or adjusted under 35 U.S.C. 154(b) by 0 days.

(21) Appl. No.: 14/191,980

(22) Filed: Feb. 27, 2014

(51) Int. Cl.
| | |
|---|---|
| A61K 36/534 | (2006.01) |
| A01N 25/34 | (2006.01) |
| A61K 8/00 | (2006.01) |
| A61K 9/00 | (2006.01) |
| A61K 36/61 | (2006.01) |
| A61K 36/752 | (2006.01) |
| A01N 65/44 | (2009.01) |
| A01N 65/06 | (2009.01) |
| A01N 65/08 | (2009.01) |
| A01N 65/20 | (2009.01) |
| A01N 65/22 | (2009.01) |
| A01N 65/28 | (2009.01) |

(52) U.S. Cl.
CPC ............. *A01N 65/44* (2013.01); *A01N 65/06* (2013.01); *A01N 65/08* (2013.01); *A01N 65/20* (2013.01); *A01N 65/22* (2013.01); *A01N 65/28* (2013.01)

(58) Field of Classification Search
CPC ..... A61K 36/28; A61K 36/185; A61K 36/42; A61K 36/03; A61K 36/15; A61K 36/287; A61K 36/899
See application file for complete search history.

(56) References Cited

U.S. PATENT DOCUMENTS

| | | | |
|---|---|---|---|
| 5,621,013 A | 4/1997 | Beldock et al. | |
| 5,942,482 A | 8/1999 | Zocchi et al. | |
| 5,985,814 A | 11/1999 | Zocchi et al. | |
| 7,666,451 B2 | 2/2010 | Mazzio et al. | |
| 8,574,628 B2 | 11/2013 | Scholl et al. | |
| 2006/0182775 A1* | 8/2006 | Everett | 424/405 |
| 2007/0098750 A1 | 5/2007 | Bessette | |
| 2007/0190094 A1 | 8/2007 | Bessette | |
| 2007/0264297 A1 | 11/2007 | Scialdone et al. | |
| 2008/0166415 A1 | 7/2008 | Markus et al. | |
| 2008/0305054 A1 | 12/2008 | Vielhaber et al. | |
| 2009/0069407 A1* | 3/2009 | Gries et al. | 514/432 |
| 2010/0196520 A1* | 8/2010 | Elraz | 424/736 |
| 2010/0286102 A1 | 11/2010 | Vielhaber | |
| 2011/0070322 A1 | 3/2011 | Bessette et al. | |
| 2011/0300083 A1 | 12/2011 | Yontz et al. | |
| 2012/0148508 A1 | 6/2012 | Thfoin et al. | |
| 2013/0142893 A1 | 6/2013 | Bessette et al. | |
| 2013/0156839 A1* | 6/2013 | Messina et al. | 424/410 |
| 2013/0280409 A1 | 10/2013 | Mushock et al. | |
| 2013/0330292 A1 | 12/2013 | Lei et al. | |

FOREIGN PATENT DOCUMENTS

| | | |
|---|---|---|
| WO | 0224857 A1 | 3/2002 |
| WO | 2006045760 A1 | 5/2006 |
| WO | 2006053912 A1 | 5/2006 |
| WO | 2007042078 A1 | 4/2007 |
| WO | 2007128725 A1 | 11/2007 |
| WO | 2010088645 A2 | 8/2010 |
| WO | WO2010088645 A * | 8/2010 |
| WO | 2013050967 A1 | 4/2013 |
| WO | WO2013050967 A * | 4/2013 |
| WO | 2013087548 A2 | 6/2013 |
| WO | 2013087549 A1 | 6/2013 |
| WO | 2013087550 A1 | 6/2013 |

OTHER PUBLICATIONS

Trongtokit et al. (2005) Phytother. Res. 19, 303-309.*
Revay et al. (2013) Acta Tropica 125; 226-230.*
Park et al. (2005) J. Amer. Mosquito Control Assoc., 21(1): 80-83.*
Nerio et al. (2010) Bioresource Technology 101; 372-378.*
Website document entitled: "Natural Homemade Mosquito Repellent as Effective as DEET" (available at http://www.homemadehints.com/homemade-mosquito-repellent). Archived to Nov. 16, 2013. Downloaded from website Jul. 28, 2014.*
Leng et al. (2012) Florida Entomologist, 95(4): 1040-1047.*
Website document entitled "How to make Homemade Essential Oil Insect Repellent Spray" (available at http://tasty-yummies.com/2013/07/17/homemade-essential-oil-insect-repellent-spray). Dated Jul. 2013. Downloaded from website Jul. 28, 2014.*
Website document entitled: "Eartheasy, solutions for sustainable living". Indicating the specific components of the commerical insect repellent Herbal Armor. Downloaded from website Jul. 28, 2014.*
Gillij et al. (2008) Bioresource Technology 99, 2507-2515.*
Fradin et al. (2002) NEJM vol. 347, No. 1, 13-18.*
Website document entitled: "Bug repellent Sunscreen" (available at http://www.badgerbalm.com/p-466-bug-repellent-sunscreen-spf-34.aspx). Archived to Apr. 27, 2013. Downloaded from website Jul. 28, 2014.*
Eller et al. (2014) Environmental Entomology, 43(3): 762-766.*
Yang et al. (2004) J. Medical Entomology, 41(4): 699-704.*

* cited by examiner

*Primary Examiner* — Chris R Tate
*Assistant Examiner* — Russell Fiebig
(74) *Attorney, Agent, or Firm* — Nancy Jack; Jeffrey Busch

(57) ABSTRACT

The present invention generally includes a blend of a blend of cedar oil, geranium oil, peppermint oil, rosemary oil, and lavender oil together with inert ingredients including water, vegetable glycerin, and isopropyl alcohol. The general mixture is enhanced for use on humans with the addition of clove oil, lemongrass oil, citronella oil, and lemon eucalyptus oil. It is, alternatively enhanced for use on dogs with the addition of soybean oil and thyme oil. Zinc oxide and/or titanium dioxide may also be added to the mixture.

4 Claims, No Drawings

INSECT REPELLENT COMPOSITIONS

BACKGROUND OF THE INVENTION

1. Field of the Invention

The present invention relates generally to insect repellents. More particularly, the present invention relates to blends of insect repellents, and to non-toxic lotions and sprays using the blends with or without a sunscreen that may be used on humans and animals.

2. State of the Art

Insects are a considerable annoyance and health risk. In an attempt to repel insects, people have turned to widely marketed lotions and sprays (e.g. Cutters, Deep Woods Off, and Tick Garde) that contain N,N-diethyl-m-toluamide (DEET) as their active ingredient. While DEET is an effective repellent, it is not particularly pleasing in smell, may sting when applied, and has a number of harmful side effects to humans. DEET is injurious to eyes, mucous membranes, and sensitive skin. In addition, because DEET is absorbed through the skin, toxic systemic reactions may result as well. For example, in August 1989, the New York State Department of Health investigated five reports of generalized seizures that were believed to be associated with the topical application of DEET. Other symptoms and maladies associated with repeated exposure to DEET have included irritability, confusion, insomnia, encephalopathy, and coma. As a result, cautionary statements regarding use of DEET have been issued by the Centers for Disease Control and the states of New York, Connecticut, New Jersey, and Utah.

The potential hazards of using a product with DEET as an active ingredient suggests that there exists a great need for a comparable repellent product that is not dangerous to its users.

It is known that various herbal and floral extracts are useful in repelling insects. For example, patent publication number WO 2013050967 A1 discloses pest control formulations that are based on natural oils in combination with a polar aromatic solvent such as aryl alcohols, aryl-alkyl alcohols, aryl aldehydes, aryl-alkyl ketones, aryl-aryl ketones, aryl carboxylic acids, aryl esters, aryl-alkyl esters, aryl-aryl esters, aryl-alkyl ethers, and aryl-aryl ethers.

Patent publication number WO 2010/088645 A2 discloses that there are a number of essential oils or components of essential oils with insecticidal properties. Examples include the oils of cedar, cinnamon, citronella, citrus, clove, eugenol (a component of clove oil), garlic, mints, such as peppermint and spearmint, rosemary, and several others. The document also discloses that representative fragrances include floral or plant oil fragrances such as citrus, clove, eucalyptus, wintergreen, rosemary, citronella or cinnamon oil, which also possesses pesticidal and antimicrobial properties.

US published patent application number 2013/0142893 A1 discloses pesticidal compositions containing rosemary oil and/or Wintergreen oil as a contact and repellent pesticide in household applications . . . rosemary oil in an amount of about 5-20%, wintergreen oil in an amount of about 20-80%, and mineral oil in an amount of about 5-45%.

While these formulations are interesting, there remains a need for non-toxic insect repellents that are also aromatically pleasing.

SUMMARY OF THE INVENTION

An object of the invention is to provide non-toxic insect repellents.

Another object of the invention is to provide non-toxic insect repellents that are also aromatically pleasing.

The present invention generally includes a blend of a blend of cedar oil, geranium oil, peppermint oil, rosemary oil, and lavender oil together with inert ingredients including water, vegetable glycerin, and isopropyl alcohol. The general mixture is enhanced for use on humans with the addition of clove oil, lemongrass oil, citronella oil, and lemon eucalyptus oil. It is, alternatively enhanced for use on dogs with the addition of soybean oil and thyme oil. The formulations may also be mixed with natural sunscreen compounds such as zinc oxide and/or titanium dioxide.

Additional objects and advantages of the invention will become apparent to those skilled in the art upon reference to the detailed description taken in conjunction with the provided figures.

DETAILED DESCRIPTION

The composition of the invention was arrived at through extensive experimentation that included ingredients such as neem, and tea tree oil as well as cedar oil, geranium oil, peppermint oil, rosemary oil, lavender oil, clove oil, lemongrass oil, citronella oil, lemon eucalyptus oil, soybean oil and thyme oil all in various concentrations together with inert ingredients including dispersants and preservatives.

It was found that some combinations were more effective against biting flies and mosquitos than other combinations or single ingredients. Some ingredients were not EPA approved and were thus disqualified. It was discovered that recent studies show that geranium oil is as effective as DEET in repelling lone star ticks, but the scent of geranium oil can be overpowering. Other ingredients were chosen based on either controlled studies and/or anecdotal evidence. For example, there is empirical evidence that soybean oil is an effective repellant. However, it is greasy and can be an allergen to some people.

All of those factors were considered in choosing the presently preferred formulation. The chosen ingredients are described for reference as follows.

Clove oil is an essential oil from the clove plant, *Syzygium aromaticum*. It is a natural analgaesic and antiseptic used primarily in dentistry for its main ingredient eugenol. It can also be purchased in pharmacies over the counter, as a home remedy for dental pain relief, mainly toothache. It is also often found in the aromatherapy section of health food stores and used in the flavoring of some medicines. Clove oil is widely used in microscopical preparation, since it is miscible with Canada balsam and has a similar refractive index to glass. Oil of cloves (usually listed as clove oil) is also used as an ingredient in cat deterrent sprays coupled with garlic oil and Sodium Lauryl Sulfate and other ingredients. Clove oil used in the formulation of the invention may or may not take the form of the organic molecule shown below:

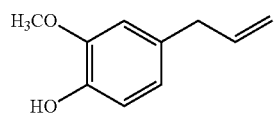

Cedar oil, also known as cedarwood oil, is an essential oil derived from the foliage, and sometimes the wood and roots, of various types of conifers, most in the pine or cypress botanical families. It has many uses in medicine, art, industry and perfumery, and while the characteristics of oils derived from various species may themselves vary, all have some degree of bactericidal and pesticidal effects. Cedar oil used in the formulation of the invention may or may not take the form of the organic molecule shown below:

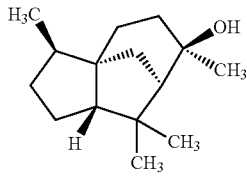

Geranium oil, geraniol, also called rhodinol, is one of the active compounds in geranium. It is a monoterpenoid and an alcohol. It is the primary part of oil-of-rose and palmarosa oil. It appears as a clear to pale-yellow oil which is insoluble in water, but soluble in most common organic solvents. It has a rose-like scent and is commonly used in perfumes. It is used in flavors such as peach, raspberry, grapefruit, red apple, plum, lime, orange, lemon, watermelon, pineapple, and blueberry. Geranium oil used in the formulation of the invention may or may not take the form of the organic molecule shown below:

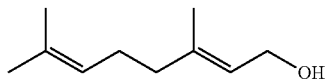

Peppermint oil, peppermint extract is an herbal extract of peppermint (*Mentha x piperita*) made from the essential oils of peppermint leaves. It is commonly used in cooking, as a dietary supplement, and as an herbal or alternative medicine. The liquid is obtained by extracting the oils from dried or fresh leaves and the flowering tops of the plant using alcohol.

Medicinal uses of peppermint extract are now well documented (see main peppermint article). Peppermint extract is also commonly used to soothe symptoms of the common cold and the flu, and as a digestive aid which may relieve bloating and flatulence. It may also be used to aid in the relief of pain from menstrual cramp and tension headaches. Because of its cooling properties, it may also relieve itching when applied topically.

Additionally, peppermint extract is believed to have antiviral and medicinal properties which may help in the treatment of herpes and the disintegration of gallstones. Peppermint oil used in the formulation of the invention may or may not take the form of the organic molecules shown below:

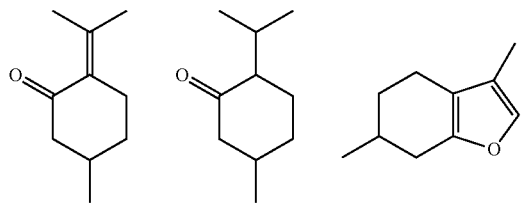

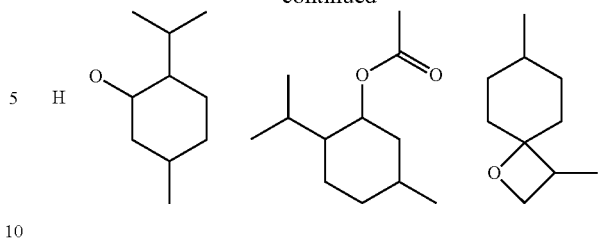

Rosemary oil has the active ingredient camphor, a white transparent waxy crystalline solid with a strong penetrating pungent aromatic odor. It is a terpenoid with the chemical formula $C_{10}H_{16}O$. It is found in wood of the camphor laurel (*Cinnamonum camphora*), a large evergreen tree found in Asia (particularly in Borneo and Taiwan, hence its alternate name) and some other related trees in the laurel family, notably *Ocotea usambarensis*; it can also be synthetically produced from oil of turpentine. It is used for its scent, as an ingredient in cooking (mainly in India), as an embalming fluid, in religious ceremonies and for medicinal purposes. Some folk remedies state camphor will deter snakes and other reptiles due to its strong odor. Similarly, camphor is believed to be toxic to insects and is thus sometimes used as a repellent. Camphor crystals are sometimes used to prevent damage to insect collections by other small insects. Rosemary oil used in the formulation of the invention may or may not take the form of the organic molecules shown below:

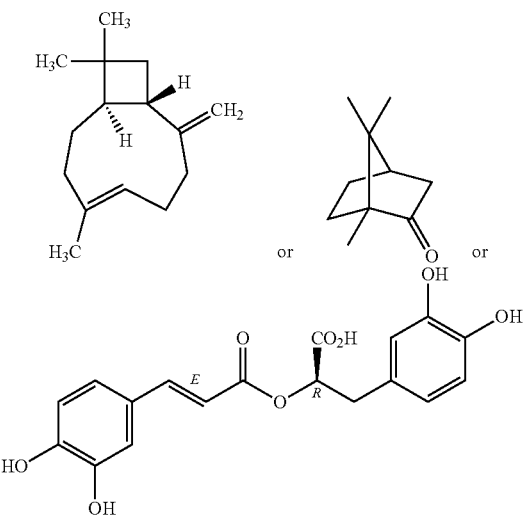

Lavender oil, which has long been used in the production of perfume, can also be used aromatherapeutically. The scent has a calming effect which may aid in relaxation and the reduction of anxiety. It may also help to relieve pain from tension headache when breathed in as vapour or diluted and rubbed on the skin. When added to a vapouriser, lavender oil may aid in the treatment of cough and respiratory infection. Lavender oil may also be used as a mosquito repellent when worn as perfume or when added to lotions or hair products. As a treatment for head lice, 5-10 drops of oil can be diluted in water to produce a hair rinse, while a few drops of undiluted oil can be added to a fine comb to eliminate nits. Lavendar oil used in the formulation of the invention may or may not take the form of the organic molecules shown below:

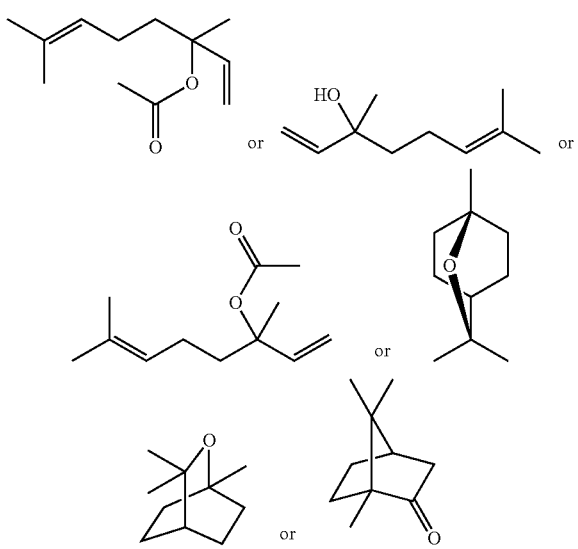

Lemongrass oil, used as a pesticide and preservative, is put on the ancient palm-leaf manuscripts found in India as a preservative. It is used at the Oriental Research Institute Mysore, the French Institute of Pondicherry, the Association for the Preservation of the Saint Thomas Christian Heritage in Kerala, and many other manuscript collections in India. The lemon grass oil also injects natural fluidity into the brittle palm leaves, and the hydrophobic nature of the oil keeps the manuscripts dry so that the text is not lost to decay due to humidity. Lemongrass oil used in the formulation of the invention may or may not take the form of the organic molecules shown below:

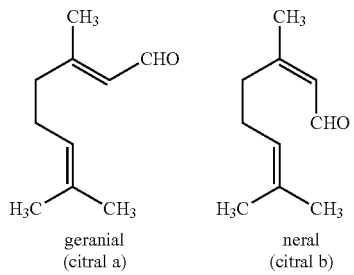

geranial (citral a)   neral (citral b)

Citronella oil, is one of the essential oils obtained from the leaves and stems of different species of *Cymbopogon* (lemongrass). The oil is used extensively as a source of perfumery chemicals such as citronellal, citronellol and geraniol. These chemicals find extensive use in soap, candles and incense, perfumery, cosmetic and flavouring industries throughout the world. Citronella oil is also a plant-based insect repellent, and has been registered for this use in the United States since 1948. The United States Environmental Protection Agency considers oil of citronella as a biopesticide with a non-toxic mode of action. Citronella oil used in the formulation of the invention may or may not take the form of the organic molecules shown below:

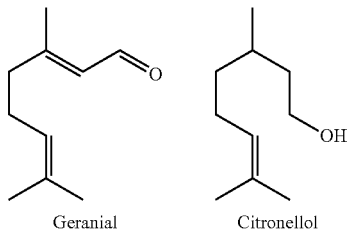

Geranial   Citronellol

Lemon eucalyptus oil: p-Menthane-3,8-diol, also known as para-menthane-3,8-diol, PMD, or Menthoglycol, is an active ingredient used in insect repellents. It smells similar to menthol and has a cooling feel. PMD is found in small quantities in the essential oil from the leaves of *Eucalyptus citriodora*. This tree is native to Australia, but is now cultivated in many warm places around the world.

*E. citriodora* oil, when refined to increase its PMD content for use in insect repellents, is known in the United States as oil of lemon eucalyptus (OLE) or by the tradename *Citriodiol*. Some commercial PMD products are not made from *E. citriodora* oil, but rather from synthetic citronellal. Pure PMD has proven to be significantly less efficacious in repelling mosquitoes than naturally derived PMD in the form of OLE.

Studies have shown that naturally-derived PMD is as effective as DEET when used in like quantities. The lemon eucalyptus oil used in the formulation of the invention may or may not take the form of the organic molecules shown below:

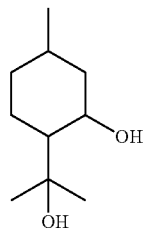

Soybean oil is a vegetable oil extracted from the seeds of the soybean (*Glycine max*). It is one of the most widely consumed cooking oils. As a drying oil, processed soybean oil is also used as a base for printing inks (soy ink) and oil paints. While soybean oil has no direct insect repellent activity, it is used as a fixative to extend the short duration of action of essential oils such as geranium oil in several commercial products. Soybean oil used in the formulation of the invention may or may not take the form of the organic molecules shown below:

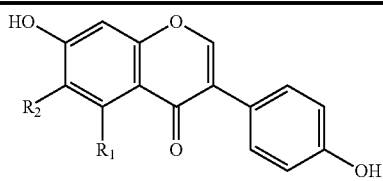

| Compounds | $R_1$ | $R_2$ |
|---|---|---|
| Daidzein | H | H |
| Glycitein | H | $OCH_3$ |
| Genistein | OH | H |

Thyme oil, the essential oil of common thyme (*Thymus vulgaris*), contains 20-54% thymol. Thyme essential oil also contains a range of additional compounds, such as p-Cymene, myrcene, borneol and linalool. Thymol, an antiseptic, is the main active ingredient in various commercially produced mouthwashes such as Listerine. Before the advent of modern antibiotics, oil of thyme was used to medicate bandages. Thymol has also been shown to be effective against various fungi that commonly infect toenails. Thymol can also be found as the active ingredient in some all-natural, alcohol-free hand sanitizers. A tea made by infusing the herb in water can be used for coughs and bronchitis. One study by Leeds Metropolitan University found that thyme may be beneficial in treating acne.

Thymol has also been used as a rapidly degrading, non-persisting pesticide. It may or may not take the form of the organic molecule shown below:

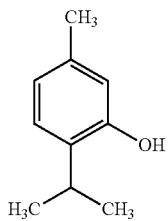

As summarized above, a first formulation according to the invention is prepared to be used as a spray for humans on skin or clothing. The presently preferred mixture is shown below in Table 1.

TABLE 1

| Ingredient | % by weight |
|---|---|
| Clove Oil | 1 |
| Cedar Oil | 1 |
| Geranium Oil | 0.5 |
| Lemongrass Oil | 1 |
| Peppermint Oil | 1 |
| Citronella Oil | 1 |
| Rosemary Oil | 1 |
| Lemon Eucalyptus Oil | 0.98 |
| Lavender Oil | 0.98 |
| Inert Ingredients including water, vegetable glycerin, and isopropyl alcohol | 91.54 |

Further, as summarized above, a second formulation according to the invention is prepared to be used as a spray for dogs. Because dogs are liable to lick their fur and ingest a repellent, ingredients were examined for toxicity if ingested by a dog. It was discovered that clove oil is highly toxic to dogs if ingested and it was therefore removed from the formula for dogs. It was also known that lemon scent is often used as a training deterrent for dogs and that they instinctively avoid it. Therefore all ingredients with a lemony scent; citronella, lemongrass and lemon eucalyptus were removed from the dog formula. It was deemed desirable to add an ingredient specifically demonstrated to combat flea infestations. After some research, it was decided to include thyme oil in the formula. However, since thyme oil has an unpleasant and overpowering scent, it was included in a lower concentration of 0.5%. It was also decided to include 2% of soybean oil as there is evidence to support its effectiveness and because the concerns about greasiness and allergens were less applicable when it came to a repellent for dogs.

The presently preferred mixture for use on dogs is shown below in Table 2.

TABLE 2

| Ingredient | % by weight |
|---|---|
| Soybean Oil | 2 |
| Cedar Oil | 1 |
| Geranium Oil | 0.1 |
| Thyme Oil | 0.5 |
| Peppermint Oil | 1 |
| Rosemary Oil | 1 |
| Lavender Oil | 0.98 |
| Inert Ingredients including water, vegetable glycerin, and isopropyl alcohol | 93.42 |

The inert ingredients were chosen for non-toxicity, dispersant properties, and for being natural. Thus, glycerin was chosen over polysorbate 80 to keep the oils in suspension in water. Only a very small amount of isopropyl alcohol is added as a preservative.

Appropriate ranges of the oils (clove, cedar, lemongrass, peppermint, rosemary, citronella and thyme) may be from 0.5% to 2%. Lavender and Lemon eucalyptus could range from 0.5% to 1%. Glycerin may range from 5% to 10% and Soybean oil from 2% to 5%. Isopropyl Alcohol may range from 0.1% to 1%. In the human formula, geranium may range for 0.5% to 2%. The amounts shown in the Tables are the presently preferred amounts.

The formulations of the invention may also be provided with a natural sunscreen such as zinc oxide or titanium dioxide.

Zinc oxide is an inorganic compound with the formula ZnO. It is a white powder that is insoluble in water, and it is widely used as an additive in numerous materials and products including rubbers, plastics, ceramics, glass, cement, lubricants, paints, ointments, adhesives, sealants, pigments, foods (source of Zn nutrient), batteries, ferrites, fire retardants, and first-aid tapes. It occurs naturally as the mineral zincite, but most zinc oxide is produced synthetically. It has a molecular form shown by example below:

$$Z=O$$

Zinc oxide is widely used to treat a variety of other skin conditions, in products such as baby powder and barrier creams to treat diaper rashes, calamine cream, anti-dandruff shampoos, and antiseptic ointments. It can be used in ointments, creams, and lotions to protect against sunburn and other damage to the skin caused by ultraviolet light (see sunscreen). It is the broadest spectrum UVA and UVB reflector that is approved for use as a sunscreen by the FDA, and is completely photostable. When used as an ingredient in sunscreen, zinc oxide sits on the skin's surface and is not absorbed into the skin, and blocks both UVA (320-400 nm) and UVB (280-320 nm) rays of ultraviolet light. Because zinc oxide and the other most common physical sunscreen, titanium dioxide, are not absorbed into the skin, they are nonirritating, nonallergenic, and non-comedogenic. It is approved for use in concentrations up to 25% although 5 to 15% is usually effective for an SPF or 20 or 30.

Titanium dioxide, also known as titanium(IV) oxide or titania, is the naturally occurring oxide of titanium, chemical formula $TiO_2$. When used as a pigment, it is called titanium white, Pigment White 6 (PW6), or CI 77891. Generally it is sourced from ilmenite, rutile and anatase. It has a wide range of applications, from paint to sunscreen to food coloring.

In cosmetic and skin care products, titanium dioxide is used as a pigment, sunscreen and a thickener. It is also used as a tattoo pigment and in styptic pencils. Titanium dioxide is produced in varying particle sizes, oil and water dispersible, and in certain grades for the cosmetic industry. It may or may not take the form of the molecule shown below:

It is used in sunscreens because of its strong UV light absorbing capabilities and its resistance to discoloration under ultraviolet light. This advantage enhances its stability and ability to protect the skin from ultraviolet light. It is approved for use in concentrations up to 25% although 5 to 5% in combination with zinc oxide is usually effective for an SPF or 20 or 30.

Thus, according to other embodiments of the invention, water is replaced in the formulations with either zinc oxide or titanium dioxide or a combination of both in concentrations of 3% to 25%.

The EPA does not allow Lemon Eucalyptus and Lavender to be listed as active ingredients in minimum risk pesticides. Both Lemon Eucalyptus and Lavender do however, have demonstrated efficacy as repellents and are therefore included at nearly the same concentration as our other active ingredients, but listed as a fragrance which they also are.

The ingredients are combined and bottled while agitating. As the mixture is not stable (i.e., it separates), agitation is necessary to keep the mixture mixed while bottling.

There have been described and illustrated herein several embodiments of insect repellent compositions. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as claimed.

What is claimed is:

1. A method of repelling insects comprising applying with a fine mist trigger sprayer an effective amount of a non-toxic, non-greasy insect repellent composition to a surface in need of repelling insects, wherein the composition consists of:
   (a) about 1% Clove Oil,
   (b) about 1% Cedar Oil,
   (c) about 1% Geranium Oil,
   (d) about 1% Lemongrass Oil,
   (e) about 1% Peppermint Oil,
   (f) about 1% Citronella Oil,
   (g) about 1% Rosemary Oil,
   (h) about 1% Lemon Eucalyptus Oil,
   (i) about 1% Lavender Oil,
   (j) water,
   (k) about 1-3% Vegetable Glycerin, and
   (l) a preservative selected from the group consisting of: isopropyl alcohol, potassium sorbate and sodium levulinate.

2. A method of repelling insects from a dog comprising applying with a fine mist trigger sprayer an effective amount of a non-toxic, non-greasy insect repellent composition to a dog in need of repelling insects, wherein the composition consists of:
   (a) about 2% Soybean Oil,
   (b) about 1% Cedar Oil,
   (c) about 1% Geranium Oil,
   (d) about 1% Peppermint Oil,
   (e) about 1% Rosemary Oil,
   (f) about 0.5% Thyme Oil,
   (g) about 1% Lavender Oil,
   (h) water,
   (i) about 1-3% Vegetable Glycerin, and
   (j) a preservative selected from the group consisting of: isopropyl alcohol, potassium sorbate and sodium levulinate.

3. The method of claim 1, wherein said effective amount is from 0.1 mL to 0.5 mL of said composition.

4. The method of claim 1, wherein said surface is selected from the group consisting of hair, fur, fabrics, vegetation and camping gear, and wherein the composition is applied without wetting, staining or damaging the surface.

* * * * *